(12) United States Patent
Boerner et al.

(10) Patent No.: US 9,157,023 B2
(45) Date of Patent: Oct. 13, 2015

(54) LIGHT-EMITTING DEVICE WITH AN IRIDIUM COMPLEX

(75) Inventors: Herbert Friedrich Boerner, Aachen (DE); Helga Hummel, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1655 days.

(21) Appl. No.: 10/579,413

(22) PCT Filed: Nov. 8, 2004

(86) PCT No.: PCT/IB2004/052328
§ 371 (c)(1),
(2), (4) Date: Feb. 20, 2007

(87) PCT Pub. No.: WO2005/049762
PCT Pub. Date: Jun. 2, 2005

(65) Prior Publication Data
US 2008/0030125 A1   Feb. 7, 2008

(30) Foreign Application Priority Data
Nov. 18, 2003 (EP) .................................. 03104258

(51) Int. Cl.
| H01J 1/62 | (2006.01) |
| C09K 11/06 | (2006.01) |
| C07F 15/00 | (2006.01) |
| H01L 51/00 | (2006.01) |
| H01L 51/50 | (2006.01) |

(52) U.S. Cl.
CPC ............. *C09K 11/06* (2013.01); *C07F 15/0033* (2013.01); *H01L 51/0085* (2013.01); *C09K 2211/1029* (2013.01); *C09K 2211/185* (2013.01); *H01L 51/5016* (2013.01); *H01L 51/5036* (2013.01)

(58) Field of Classification Search
None
See application file for complete search history.

(56) References Cited

U.S. PATENT DOCUMENTS

| 2003/0141809 A1* | 7/2003 | Furugori et al. .............. 313/504 |
| 2004/0076853 A1* | 4/2004 | Jarikov ......................... 428/690 |
| 2004/0166364 A1* | 8/2004 | Kathirgamanathan ........ 428/690 |

FOREIGN PATENT DOCUMENTS

| EP | 1434469 A1 | 6/2004 |
| EP | 1359790 B1 | 10/2008 |
| JP | 2001345183 A | 12/2001 |
| JP | 2003007467 A * | 1/2003 ............ H05B 33/14 |
| KR | 2002076545 A | 10/2002 |

(Continued)

OTHER PUBLICATIONS

JP 2003007467 A machine English translation. Translated Dec. 31, 2009.*

(Continued)

*Primary Examiner* — J. L. Yang

(57) ABSTRACT

The invention relates to a light-emitting device comprising at least a substrate, an anode, a light-emitting layer and a cathode whereby the light-emitting layer contains an iridium complex $IrL_3$ and whereby at least two ligands L are a dibenzoquinoline. The invention relates in particular to the complexes Ir(dibenzo[f,h]quinoline)$_2$(pentane-2,4-dionate) and Ir(dibenzo[f,h]quinoline)$_3$ which emit light with a wavelength of $\lambda_{max}$=545 nm and $\lambda_{max}$=595 nm respectively.

15 Claims, 2 Drawing Sheets

(56) References Cited

FOREIGN PATENT DOCUMENTS

| WO | WO 02/102924 A2 * | 12/2002 | ............ C09K 11/06 |
|---|---|---|---|
| WO | 2006090301 A1 | 8/2006 | |
| WO | 2007095118 A2 | 8/2007 | |
| WO | 2009100991 A1 | 8/2009 | |

OTHER PUBLICATIONS

JP 2003-007467 A machine English translation. Translated Dec. 31, 2009.*

Lamansky et al., "Synthesis and characterization of phosphorescent cyclometalated iridium complexes", 2001, pp. 1704-1711, vol. 40.

Lamansky et al., "Cyclometalated Ir complexes in polymer organic light-emitting devices", Journal of Applied Physics, American Institute of Physics, Aug. 2002, pp. 1570-1575, vol. 92, New York.

Nicolaides et al., "Diels-Alder Reactions of Ethyl [10-(Methoxyimino)phenanthren-9-ylidene]acetate with Dienophiles, Synthesis of Dibenzo[f,h]quinoline and Dibenzo[a,c]acridine Derivatives", J. Org. Chem., 1994, pp. 629-634, vol. 95.

Wilde et al., "Resolution and analysis of the components in dual emission of mixed-chelate/ortho-metalate complexes of indium(III)", J. Phys. Chem., 1991, pp. 629-634, vol. 95.

Ichimura et al, "Excited-state absorption spectroscopy of ortho-metalated Ir(III) complexes", J. Phys. Chem., 1987, pp. 6104-6106, vol. 91.

* cited by examiner

LIGHT-EMITTING DEVICE WITH AN IRIDIUM COMPLEX

The invention relates to a light-emitting device, comprising at least a substrate, an anode, a light-emitting layer and a cathode. The invention also relates to iridium complexes.

Electronically activated display systems are known and widespread in different embodiments based on various principles.

One principle uses organic light-emitting diodes, so-called OLEDs, as a light source. Organic light-emitting diodes are created from several function layers. "Philips Journal of Research, 1998, 51, 467" contains a description of a typical structure of an OLED. A typical structure comprises a layer of ITO (indium tin oxide) as a transparent electrode (anode), a conductive polymer layer, an electroluminescent layer, i.e. a layer with a light-emitting material, and an electrode (cathode) made from a metal, preferably a metal with a low work function. A structure such as this is applied on a substrate, generally glass. The light which is generated reaches the observer through the substrate.

A light-emitting polymer, for example, may be used as the light-emitting material. An OLED with a light-emitting polymer in the electroluminescent layer is called a polyLED or PLED.

However, an OLED can also contain small light-emitting molecules serving as light-emitting material in the electroluminescent layer. An OLED with small light-emitting molecules in the electroluminescent layer is called a SMOLED (Small Molecule Organic Light Emitting Diode). In this embodiment the light-emitting materials are generally embedded in a matrix comprising a hole or electron-transporting material.

Holes and electrons meet and re-combine in the electroluminescent layer. Consequently, the light-emitting material is activated either directly or via energy transfer. The excited, light-emitting material returns to its basic state under light emission.

Iridium complexes are particularly suitable as light-emitting materials. Colors ranging from bluish green to red are generated by varying the ligands in the iridium complexes.

The human eye is at its most sensitive at a wavelength of 555 nm (green light). The sensitivity of the eye decreases at radiation of a greater wavelength (red) as well as of a shorter wavelength (blue). The sensitivity of the eye for red light (650 nm) is only a tenth of its sensitivity for green light (555 nm). In other words, it takes ten times as much red light as green light to achieve the same illuminance.

Consequently, in order to use an OLED as a source for white light, it is desirable to use iridium complexes which emit in the orange spectral range because the human eye is more sensitive there than in the red spectral range.

There is a constant need for new electroluminescent compounds with improved efficiency.

Consequently, it is an object of the invention to provide a light-emitting device which contains an improved iridium complex in the light-emitting layer.

This object is achieved by means of a light-emitting device comprising at least a substrate, an anode, a light-emitting layer and a cathode whereby the light-emitting layer contains an iridium complex $IrL_3$ and whereby at least two ligands L are a dibenzoquinoline.

Dibenzoquinolines are large, rigid molecules with good complexing properties. An iridium complex with at least two dibenzoquinolines is very stable, making it suitable to use in the light-emitting layer of a light-emitting device.

There are other advantageous embodiments in the dependent claims.

Furthermore, the invention also relates to iridium complex $IrL_3$ in which at least two ligands L are a dibenzoquinoline. The invention rela-s to the iridium complexes Ir(dibenzo[f,h]quinoline)$_2$(pentane-2,4-dionate) and Ir(dibenzo[f,h]quinoline)$_3$, in particular.

These and other aspects of the invention are apparent from and will be elucidated with reference to the three Figures and five embodiments described hereinafter.

Figure 1:
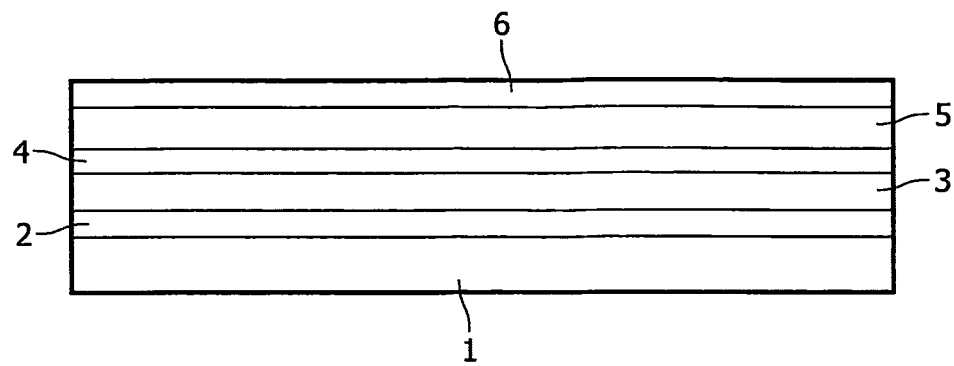
FIG. 1 shows the cross-section of a light-emitting device.

A light-emitting device possesses a substrate 1 and, mounted on it, at least one anode 2, a light-emitting layer 4 and a cathode 6. In order to improve the efficiency of a light-emitting device, it may, as FIG. 1 shows, additionally possess a hole-transporting layer 3 between the anode 2 and the light-emitting layer 4, as well as an electron-transporting layer 5 between the cathode 6 and the light-emitting layer 4.

The substrate 1 is preferably a transparent glass plate or a transparent plastic plate. The plastic plate may contain polyethylene terephthalate (PET), for example. The anode 2 is preferably transparent and may contain p-doped silicon, indium-doped tin oxide (ITO) or antimony-doped tin oxide (ATO), for example. The anode 2 ideally contains ITO. The anode 2 is not structured, it possesses a flat design. The cathode 6 may contain a metal, such as aluminum, copper, silver or gold, an alloy or n-doped silicon, for example. It may be preferable for the cathode 6 to possess two or more conductive layers. It may be particularly preferable for the cathode 6 to possess a first layer made from an alkaline-earth metal, such as calcium or barium, or from an alkali halide, such as LiF or lithium benzoate, and a second layer made from aluminum. The cathode 6 may be structured and, for example, possess a number of parallel strips of the conductive material(s). Alternatively, the cathode 6 may not be structured and may have a flat design.

The anode 2 is bordered by a first hole-transporting layer 3 which simplifies the injection and transport of the holes into the device. Suitable materials for the hole-transporting layer 3 are, for example, triaryl amine, diaryl amine, tristilbene amine or a mix of polyethylene dioxythiophene (PDOT) and poly(styrene sulphonate).

Positioned between the cathode 6 and the light-emitting layer 4 there is an electron-transporting layer 5, which may possess tris-(8-hydroxy-quinolato)-aluminum ($Alq_3$), 1,3,5-tris-(1-phenyl-1H-benzimidazole-2-yl)benzole (TPBI) or low-electron heterocycles, such as 1,3,4-oxadiazoles or 1,2,4-triazoles.

The light-emitting layer 4 contains one or more of the new iridium complexes as light-emitting material.

The iridium complexes $IrL_3$ in accordance with the invention are neutral and non-ionic. At least two of the three ligands L are a dibenzoquinoline. Alternatively, all three of the ligands L are a dibenzoquinoline. The ligands L are preferably identical dibenzoquinohnes. However, they may also be different.

Dibenzoquinolines are quinolines to which two other benzole rings are condensed. Examples of suitable dibenzoquinolines are dibenzo[f,h]quinoline (dbzq), dibenzo[c,f]quinoline, dibenzo[c,d,e]quinoline or dibenzo[f,g]quinoline. All these dibenzoquinolines are large, rigid ligands with good complexing properties. Dibenzo[f,h]quinoline is the preferred ligand on account of its sterics.

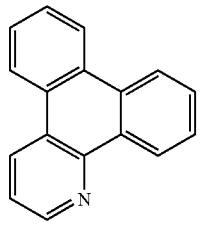

I

The dibenzoquinolines can additionally possess other substituents R. Each ring can possess one or more substituents R which influence the electronic properties of the dibenzoquinoline and, thus, of the later iridium complex.

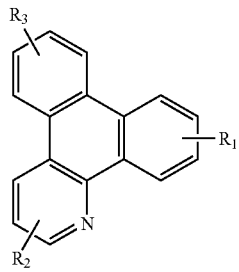

Ia

The substituents $R_1$, $R_2$, $R_3$, etc. may, for example, contain linear or branched $C_1$-$C_8$-alkyl groups, $C_2$-$C_6$-alkenyl groups, $C_3$-$C_8$-cycloalkyl groups, $C_1$-$C_6$-alkinyl groups, aryl groups, heteroaryl groups, $C_1$-$C_6$-heterocycloalkyl groups, amines, phosphates, phosphine groups, phosphine oxide groups, halogens, sulphate groups, sulphonate groups, sulphone groups, carboxylates, $C_2$-$C_6$-alkoxyl groups, phosphate groups, etc. The substituents $R_1$, $R_2$, $R_3$, etc. may be identical or different.

If the iridium complex contains two dibenzoquinolines as ligands L, the third ligand L is preferably the anion of a 1.3-diketone derivatives:

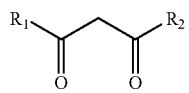

II

The substituents $R_1$ and $R_2$ etc. may, for example, contain linear or branched $C_1$-$C_8$-alkyl groups, $C_2$-$C_6$-alkenyl groups, $C_3$-$C_8$-cycloalkyl groups, $C_1$-$C_6$-alkinyl groups, aryl groups, heteroaryl groups, $C_1$-$C_6$-heterocycloalkyl groups, amines, phosphates, phosphine groups, phosphine oxide groups, halogens, sulphate groups, sulphonate groups, sulphone groups, carboxylates, $C_2$-$C_6$-alkoxyl groups, phosphate groups, etc. The substituents $R_1$ and $R_2$ may be identical or different.

The third ligand L is preferably selected from the following group: pentane-2,4-dionate (acac), 2,2,6,6-tetramethyl-3,5-heptane dionate (thd), 7,7-dimethyl-1,1,1,2,2,3,3-heptafluorine-4,6-octane dionate (fod), 1,1,1,5,5,5-hexafluoropentane-2,4-dionate (hfa), 4,4,4-trifluoro1-(2-thienyl)butane-1,3-dionate (ttfa), 1,3-diphenyl propane-1,3-dionate (dbm), 4,4,4-trifluorine-1-(2-naphthyl)butane-1,3-dionate (tfnb) and 4,4,4-trifluoro-1-(1-napthyl)butane-1,3-dionate. They are all well known ligands with good complexing properties. Pentane-2,4-dionate (acac) is the ligand which is most preferred.

A preferred iridium complex is Ir(dibenzo[f,h]quinoline)$_2$ (pentane-2,4-dionate).

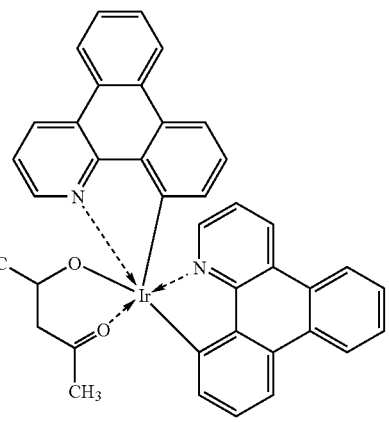

III

Another preferred iridium complex is Ir(dibenzo[f,h]quinoline)$_3$.

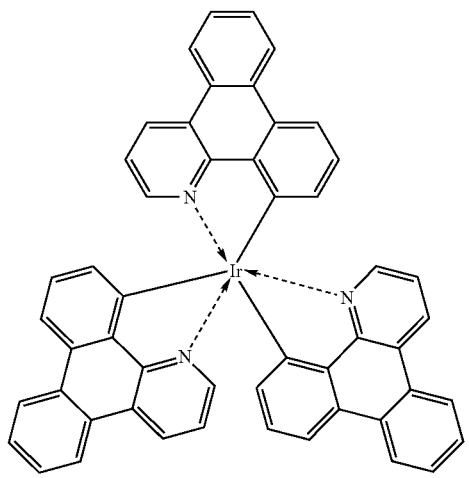

IV

Both complexes emit light with a wavelength of λ<600 nm. Complex IV emits light with a wavelength $\lambda_{max}$ of 595 nm (in methyl-THF) while complex III emits lights with a wavelength $\lambda_{max}$ of 545 nm (in methyl-THF).

Given the fact that, as has been indicated above, the human eye is most sensitive at a wavelength of 555 nm, light-emitting devices with complex III and/or complex IV in the light-emitting layer 4 exhibit favorable energy-efficiency.

It is surprising to note that a shift in emission wavelength $\lambda_{max}$ of 50 nm as achieved by simply varying a ligand, for example by replacing a dibenzo[f,h]chinoline with pentane-2,4-dionate.

It is also advantageous that, given their structural similarity, complexes III and IV also possess similar physical properties, thereby simplifying the manufacture and operation of a light-emitting device which contains two or more iridium complexes in accordance with the invention in the light-emitting layer 4. Undesired chemical interactions between two different complexes, such as ligand exchange reactions, make no difference here either. This is particularly advantageous in the case of devices which emit white light because the light-emitting layer 4 in them contains several light-emitting materials, which emit in the three primary colors for example.

In order to produce complexes in accordance with the invention with three dibenzoquinolines as ligand L, an iridium salt, such as $IrCl_3$ or $Ir(acac)_3$ is converted with the corresponding dibenzoquinoline in a suitable solvent.

The synthesis of von $Ir(dbzq)_3$ led to a fac/mer isomer mix in the case of all synthesis pathways. The prefixes fac- and mer-indicate that there are three identical ligands immediately adjacent to one another in octahedral coordination compounds with different ligands.

In this case, while the complexes with three identical dibenzoquinolines as ligands L possess three identical ligands, each of the dibenzoquinolines has two different coordination sites: One coordinates a dibenzoquinoline via the nitrogen to the iridium(III) cation, and a covalent bond between a C-atom on one of the aromatic rings and the Ir(III) cation. This means in arguments to the contrary that only dibenzoquinolines which can form an N—Ir and a C—Ir bond can be used as ligands.

fac/mer isomerism exists in these complexes in terms of the close proximity between the three identical coordination sites.

In order to produce complexes in accordance with the invention with two dibenzoquinolines as ligands L, the dichlorine-bridged dimer $(dibenzoquinohne)_2Ir(\mu-Cl)_2(dibenzoquinoline)_2$ is produced first, based on $IrCl_3$. The dichlorine-bridged dimer $(dibenzoquinoline)_2Ir(\mu-Cl)_2(dibenzoquinoline)_2$ is then converted into the required iridium complex with the third ligand, for example a 1,3-diketone derivative, such as pentane-2,4-dione, in the presence of a base.

Vacuum separation is used to obtain thin films of the iridium complexes in accordance with the invention which possess good electroluminescent properties. By varying the ligands L or substituents R in the dibenzoquinolines, the electroluminescent properties of the light-emitting materials can be finely coordinated.

The iridium complexes can be used on their own (accounting for 100% of the total weight of the light-emitting layer 4) or embedded in a matrix comprising hole or electron-transporting material in the light-emitting layer 4. The quantity of iridium complex is preferably >10% (of the total weight of the light-emitting layer 4). The choice of matrix material depends on the requirements of the iridium complex. For example, the matrix may contain 4,4',4"-tri(N-carbazolyl)triphenyl amine (TCTA), 2,9-dimethyl-4,7-diphenyl-1,10-phenanthroline (BCP) or 1,3,5-tris-(1-phenyl-1H-benzimidazole-2-yl)benzole (TPBI).

The following embodiments are examples and are intended to illustrate the invention, but not limit it.

EMBODIMENT 1

Synthesis of the Dichlorine-Bridged Dimer $(dbzq)_2Ir(\mu-Cl)_2(dbzq)_2$ 250 mg of $IrCl_3 \cdot 3H_2O$ and 407 mg of dibenzo[f,h]quinoline (dbzq) were dissolved in a mixture of 2-ethoxy ethanol (20 ml) and water (7 ml) and were heated and refluxed for 24 hours. After cooling down to room temperature, the yellow deposit which was obtained was centrifuged off, washed with ethanol (60 ml) and acetone (60 ml) and dried.

370 mg (77%) of the dichiorine-bridged dimer was obtained in the form of a yellow powder.

EMBODIMENT 2

Synthesis of $Ir(dbzq)_2(acac)$ Starting Off from $(dbzq)_2Ir(\mu-Cl)_2(dbzq)_2$ $(dbzq)_2Ir(\mu-Cl)_2(dbzq)_2$ was heated and refluxed for 20 hours with 2.5 equivalent acetyl acetonate and 400 mg of sodium carbonate in 2-ethoxy ethanol. The obtained orange-colored deposit was centrifuged off, washed with water, n-hexane, diethyl ether and ethanol. The yield of raw product was between 70 and 75%.

The raw product was cleaned in silica gel ($CH_2Cl_2$/n-hexane/diethyl ether) by means of column chromatography.

$^1$H-NMR ($CDCl_3$): δ=1.80 (s, 6H, $2CH_3$), 5.29 (s, 1H, CH), 6.33 (d, J=7.3 Hz, 2H, CH arom.), 6.97 (t, 2H, CH arom.), 7.61 (dd, J=7.7 Hz, J=5.4 Hz, 2H, CH arom.), 7.66 to 7.72 (m, 4H, CH arom.), 7.86 (d, J=8.0 Hz, 2H, CH arom.), 8.56 to 8.60 (m, 2H, CH arom.), 8.64 to 8.67 (m, 2H, CH arom.), 8.87 to 8.91 (m, 4H, CH arom.).

Figure 2:
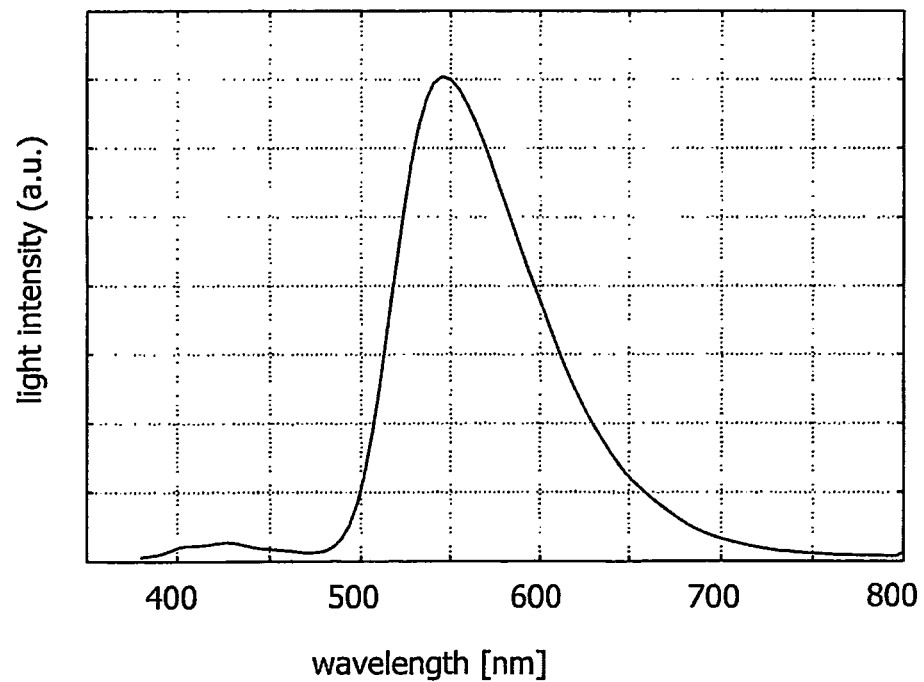
FIGS. 2 and 3 show the luminescence spectra of iridium complexes in accordance with the invention.

The complex obtained, $Ir(dbzq)_2(acac)$, emits light at a wavelength $\lambda_{max}$ of 545 nm (in methyl THF). The emission spectrum is shown in FIG. 2.

EMBODIMENT 3

Synthesis of $Ir(dbzq)_3$ 53 mg of iridium(III)acetyl acetonate and 250 mg of dibenzo[f,h]quinoline were added to 5 ml of degassed ethylene glycol. The suspension obtained was heated and refluxed for 60 hours. After cooling down to room temperature, the reaction mixture was added to 10 ml of 1N HCl. Following 5 minutes stirring, the orange-colored, crystalline deposit was filtered off, washed with 5 ml of 1N HCl and water and dried.

The product was dissolved in dichloromethane, filtered through silica gel and dried.

The $^1$H-NMR spectrum showed that the product contains mer- and fac-isomers from the complex, whereby the share of mer-isomers is larger.

Figure 3:
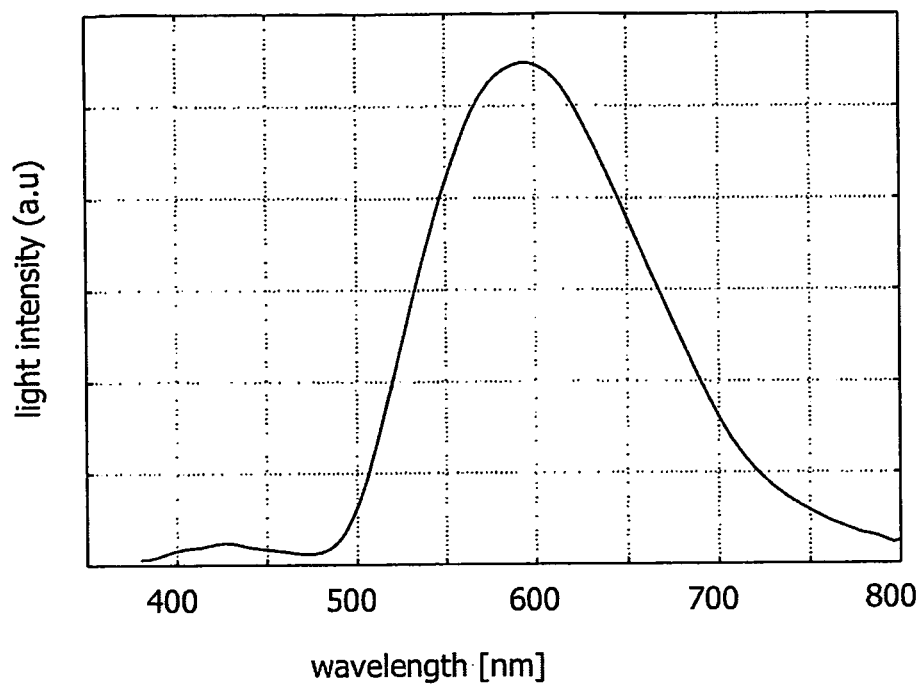

The mixture of fac/mer-isomers in the complex $Ir(dbzq)_3$ emits light at a wavelength $\lambda_{max}$ of 595 nm (in methyl THF). The emission spectrum is shown in FIG. 3.

EMBODIMENT 4

Synthesis of $Ir(dbzq)_3$ Starting Off from $Ir(dbzq)_2(acac)$ 258 mg of $Ir(dbzq)_2(acac)$ and 119 mg of dibenzo[f,h] quinoline were heated for 24 hours at 220° C. in 5 ml of glycerine. After cooling down to room temperature, the reaction mixture was diluted with water, and the deposit was centrifuged off. Following repeated washing with methanol, the deposit was dried in the vacuum.

This $^1$H-NMR spectrum also showed that the product contains mer- and fac-isomers from the complex, whereby the share of mer-isomers is larger.

EMBODIMENT 5

A 150 nm thick layer of ITO, serving as an anode 2, was applied to a transparent substrate 1 made from glass. A 30 nm thick layer of α-NPD, serving as a hole-transporting layer 3, was applied to the anode 2 by means of spin-coating. A light-emitting layer 4 made from Ir(dbzq)₂(acac), embedded in TCTA, was applied to the hole-transporting layer 3. The light-emitting layer 4 was 30 nm thick. A 40 nm thick layer of TPBI, serving as an electron-transporting layer 5, was applied to the light-emitting layer 4. A 151 nm thick cathode 6 comprising a 1 nm thick first layer of lithium benzoate and a 150 nm thick second layer of aluminum were applied to the electron-transporting layer 5.

The invention claimed is:

1. A light-emitting device, comprising:
   at least a substrate;
   an anode;
   a light-emitting layer; and
   a cathode,
   wherein the light-emitting layer includes an iridium complex IrL₃, L₃ being three ligands, and wherein two ligands of the three ligands are a dibenzoquinoline, and a third ligand of the three ligands is selected from the following group: 7,7-dimethyl-1,1,1,2,2,3,3-heptafluorine-4,6-octane dionate (fod), 1,1,1,5,5,5-hexafluoropentane-2,4-dionate (hfa), 4,4,4-trifluoro 1-(2-thienyl)butane-1,3-dionate (ttfa), 4,4,4-trifluorine-1-(2-naphthyl)butane-1,3-dionate (tfnb) and 4,4,4-trifluoro-1-(1-napthyl)butane-1,3-dionate.

2. The light-emitting device as claimed in claim 1, wherein the dibenzoquinoline is dibenzo[f,h]quinoline.

3. The light-emitting device as claimed in claim 1, wherein the light-emitting layer includes a further light-emitting material.

4. The light-emitting device as claimed in claim 3, wherein the further light-emitting material is a further iridium complex.

5. An iridium complex IrL₃, L₃ being three ligands, comprising:
   two ligands of the three ligands that are dibenzoquinolines; and
   a third ligand of the three ligands is selected from the following group: 7,7-dimethyl-1,1,1,2,2,3,3-heptafluorine-4,6-octane dionate (fod), 1,1,1,5,5,5-hexafluoropentane-2,4-dionate (hfa), 4,4,4-trifluoro 1-(2-thienyl)butane-1,3-dionate (ttfa), 4,4,4-trifluorine-1-(2-naphthyl)butane-1,3-dionate (tfnb) and 4,4,4-trifluoro-1-(1-napthyl)butane-1,3-dionate.

6. The light-emitting device according to claim 1, wherein the third ligand of the three ligands is 7,7-dimethyl-1,1,1,2,2,3,3-heptafluorine-4,6-octane dionate (fod).

7. The light-emitting device according to claim 1, wherein the dibenzoquinoline ligands include substituents R₁, R₂, R₃ according to the compound:

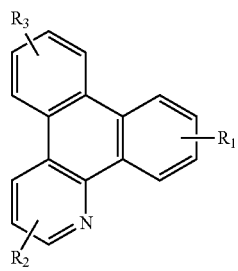

wherein the substituents R₁, R₂ and R₃ are selected from the group consisting of: linear or branched $C_1$-$C_8$-alkyl groups, $C_2$-$C_6$-alkenyl groups, $C_1$-$C_3$ cycloalkyl groups, $C_2$-$C_6$-alkynyl groups, aryl groups, heteroaryl groups, $C_1$-$C_6$-heteocycloalkyl groups, amines, phosphates, phosphine groups, phosphine oxide groups, halogens, sulphate groups, sulphonate groups, sulphone groups, carboxylates, $C_2$-$C_6$alkoxyl groups, and phosphate groups.

8. The light-emitting device according to claim 7, wherein the R₁, R₂ and R₃ substituents are different.

9. The iridium complex IrL₃ according to claim 5, wherein the third ligand of the three ligands is 7,7-dimethyl-1,1,1,2,2,3,3-heptafluorine-4,6-octane dionate (fod).

10. The iridium complex IrL₃ according to claim 5, wherein the third ligand of the three ligands is 1,1,1,5,5,5-hexafluoropentane-2,4-dionate (hfa).

11. The iridium complex IrL₃ according to claim 5, wherein the third ligand of the three ligands is 4,4,4-trifluoro 1-(2-thienyl)butane-1,3-dionate (ttfa).

12. The iridium complex IrL₃ according to 5, wherein the third ligand of the three ligands is 4,4,4-trifluorine-1-(2-naphthyl)butane-1,3-dionate (tfnb).

13. The iridium complex IrL₃ according to 5, wherein the third ligand of the three ligands is 4,4,4-trifluoro-1-(1-napthyl)butane-1,3-dionate.

14. The light-emitting device as claimed in claim 1, wherein the dibenzoquinoline is selected from the group consisting of: dibenzo[c,f]quinoline, dibenzo[c,d,e]quinoline, and dibenzo[f,g]quinoline.

15. The light-emitting device as claimed in claim 1, wherein the light-emitting layer further includes a matrix material selected from the group consisting of: 4,4',4''-tri(N-carbazolyl)triphenyl amine (TCTA), 2,9-dimethyl-4,7-diphenyl-1,10-phenanthroline (BCP) and 1,3,5-tris-(1-phenyl-1H-benzimidazole-2-yl)benzole (TPBI).

* * * * *